(12) United States Patent
Marx

(10) Patent No.: US 8,734,408 B2
(45) Date of Patent: May 27, 2014

(54) AUTOMATED EYEDROP DELIVERY SYSTEM WITH EYELID RETRACTING LEGS

(76) Inventor: Alvin J. Marx, San Antonio, TX (US)

( * ) Notice: Subject to any disclaimer, the term of this patent is extended or adjusted under 35 U.S.C. 154(b) by 404 days.

(21) Appl. No.: 12/722,340

(22) Filed: Mar. 11, 2010

(65) Prior Publication Data
US 2010/0286634 A1 Nov. 11, 2010

Related U.S. Application Data

(63) Continuation-in-part of application No. 12/319,908, filed on Jan. 12, 2009, now Pat. No. 8,246,589.

(60) Provisional application No. 61/026,471, filed on Feb. 5, 2008, provisional application No. 61/075,768, filed on Jun. 26, 2008, provisional application No. 61/086,436, filed on Aug. 5, 2008, provisional application No. 61/097,153, filed on Sep. 15, 2008.

(51) Int. Cl.
*A61M 35/00* (2006.01)
(52) U.S. Cl.
USPC .......................................... 604/298; 604/302
(58) Field of Classification Search
USPC .................................. 604/294–302
See application file for complete search history.

(56) References Cited

U.S. PATENT DOCUMENTS

| | | |
|---|---|---|
| 1,362,682 A | 12/1920 | Dayton |
| 2,219,604 A | 10/1940 | Trotter |
| 2,734,665 A | 2/1956 | Flamm |
| 3,058,466 A * | 10/1962 | Routsong ................... 604/302 |
| 3,261,355 A | 7/1966 | Burbig |
| 3,486,663 A | 12/1969 | Humphrey |
| 3,872,866 A | 3/1975 | Lelicoff |
| 3,934,590 A | 1/1976 | Campagna et al. |
| 4,085,750 A | 4/1978 | Bosshold |
| 4,111,200 A | 9/1978 | Sbarra et al. |
| 4,115,042 A | 9/1978 | Schroeder |
| 4,131,115 A | 12/1978 | Peng |
| 4,321,916 A | 3/1982 | McKee |
| 4,336,895 A | 6/1982 | Aleff |
| 4,349,133 A | 9/1982 | Christine |
| 4,386,608 A | 6/1983 | Ehrlich |

(Continued)

FOREIGN PATENT DOCUMENTS

JP 2007215962 A 8/2007

*Primary Examiner* — Melanie Hand
*Assistant Examiner* — Paula Craig
(74) *Attorney, Agent, or Firm* — Kammer Browning PLLC

(57) ABSTRACT

An eye drop bottle holder with resilient legs includes an inverted U-shaped member made from resilient injection molded plastic. The top portion of the inverted U-shaped member includes an eye drop bottle holder. The right and left leg of the U-shape each terminate in an outwardly disposed J-shape covered by a soft rubber-like pad. The user can attach an eye drop bottle to the inverted U-shaped member so that the dispensing tip of the bottle is in close proximity the user's eye. The user can cause his or her eye lid to remain open by squeezing the right and left legs together, then placing the pads on the upper and lower eye orbit, then releasing the legs causing the flesh of the user's eyelids to be spread apart. In a preferred embodiment, an electro-mechanical assembly can automatically press on the side wall of the bottle to cause a predetermined amount of solution to be dispensed. An LED light flashes (is either activated or deactivated) to show the user that a dispensing event has taken place.

4 Claims, 21 Drawing Sheets

(56) References Cited

U.S. PATENT DOCUMENTS

| | | | | |
|---|---|---|---|---|
| 4,515,294 | A | 5/1985 | Udall | |
| 4,543,096 | A | 9/1985 | Keene | |
| 4,834,727 | A | 5/1989 | Cope | |
| 4,927,062 | A | 5/1990 | Walsh | |
| 4,960,407 | A * | 10/1990 | Cope | 604/300 |
| 4,973,322 | A | 11/1990 | Jewart | |
| 4,981,479 | A | 1/1991 | Py | |
| 5,007,905 | A * | 4/1991 | Bauer | 604/295 |
| 5,030,214 | A * | 7/1991 | Spector | 604/301 |
| 5,040,706 | A | 8/1991 | Davis et al. | |
| 5,059,188 | A * | 10/1991 | Goddard | 604/300 |
| 5,064,420 | A | 11/1991 | Clarke et al. | |
| 5,215,231 | A | 6/1993 | Paczonay | |
| 5,261,571 | A | 11/1993 | Goncalves | |
| 5,366,448 | A * | 11/1994 | Basilice et al. | 604/290 |
| 5,370,267 | A | 12/1994 | Schroeder | |
| 5,382,243 | A | 1/1995 | Mulholland | |
| 5,401,259 | A | 3/1995 | Py | |
| 5,433,190 | A * | 7/1995 | Sunalp | 600/236 |
| 5,516,008 | A | 5/1996 | Rabenau et al. | |
| 5,578,020 | A | 11/1996 | Mosley | |
| 5,611,464 | A | 3/1997 | Tsao et al. | |
| 5,611,788 | A * | 3/1997 | Marchment | 604/295 |
| 5,795,342 | A | 8/1998 | Shapiro et al. | |
| 5,902,292 | A | 5/1999 | Feldman | |
| 5,993,428 | A | 11/1999 | Hardge | |
| 6,010,488 | A | 1/2000 | Deas | |
| 6,041,978 | A | 3/2000 | Hagele | |
| 6,090,086 | A * | 7/2000 | Bolden | 604/302 |
| RE37,047 | E | 2/2001 | Py | |
| 6,241,124 | B1 | 6/2001 | Hoyt | |
| 6,336,917 | B1 * | 1/2002 | Berke | 604/295 |
| 6,371,945 | B1 | 4/2002 | Sherman | |
| 6,595,970 | B1 | 7/2003 | Davidian | |
| 6,610,036 | B2 | 8/2003 | Branch et al. | |
| 6,730,066 | B1 | 5/2004 | Bennwik et al. | |
| 6,736,802 | B1 | 5/2004 | Recanati | |
| 6,814,265 | B2 | 11/2004 | Clifford et al. | |
| 7,191,916 | B2 | 3/2007 | Clifford et al. | |
| 7,235,065 | B1 | 6/2007 | Sorensen | |
| 7,296,710 | B2 * | 11/2007 | Petschner | 222/103 |
| 7,513,396 | B2 | 4/2009 | Pardes et al. | |
| 7,621,273 | B2 | 11/2009 | Morton et al. | |
| 8,246,589 | B2 * | 8/2012 | Marx | 604/302 |
| 2002/0161344 | A1 * | 10/2002 | Peclat et al. | 604/295 |
| 2004/0039355 | A1 | 2/2004 | Gonzalez et al. | |
| 2004/0111070 | A1 | 6/2004 | Hanley | |
| 2004/0173642 | A1 | 9/2004 | Clifford et al. | |
| 2004/0267214 | A1 * | 12/2004 | Kerssies | 604/299 |
| 2005/0131358 | A1 | 6/2005 | Skolik | |
| 2005/0147546 | A1 | 7/2005 | Long | |
| 2005/0261641 | A1 | 11/2005 | Warchol | |
| 2006/0079851 | A1 | 4/2006 | Guerrieri | |
| 2006/0264855 | A1 | 11/2006 | Goldenberg et al. | |
| 2007/0055208 | A1 | 3/2007 | Berger et al. | |
| 2007/0095862 | A1 | 5/2007 | Swiss et al. | |
| 2008/0208148 | A1 * | 8/2008 | Soon et al. | 604/301 |
| 2008/0233053 | A1 * | 9/2008 | Gross et al. | 424/45 |
| 2009/0236374 | A1 | 9/2009 | Pardes et al. | |
| 2009/0259204 | A1 | 10/2009 | Galdeti et al. | |
| 2009/0293870 | A1 | 12/2009 | Brunnberg et al. | |
| 2009/0318883 | A1 | 12/2009 | Sugahara et al. | |
| 2010/0022971 | A1 * | 1/2010 | Marx | 604/302 |
| 2010/0286633 | A1 | 11/2010 | Marx | |
| 2013/0006202 | A1 * | 1/2013 | Marx | 604/290 |

\* cited by examiner

AUTOMATED EYEDROP DELIVERY SYSTEM WITH EYELID RETRACTING LEGS

CROSS REFERENCE TO RELATED APPLICATIONS

This Application claims the benefit under Title 35 United States Code §120 as a Continuation-in-Part of U.S. patent application Ser. No. 12/319,908, filed Jan. 12, 2009 now U.S. Pat. No. 8,246,589; which itself further claims the benefit under Title 35 United States Code §119(e) of U.S. Provisional Patent Application Ser. No. 61/026,471, filed Feb. 5, 2008; U.S. Provisional Patent Application Ser. No. 61/075,768, filed Jun. 26, 2008; U.S. Provisional Patent Application Ser. No. 61/086,436, filed Aug. 5, 2008; and U.S. Provisional Patent Application Ser. No. 61/097,153, filed Sep. 15, 2008; the full disclosures of which are each incorporated herein by reference.

BACKGROUND OF THE INVENTION

1. Field of the Invention

This invention relates generally to the field of eye drop dispensing devices and more specifically to an eye drop bottle holder with resilient legs.

2. Description of the Related Art

Devices for dispensing eye drop solutions are known. Generally, a bottle of eye drop solution includes a drop dispenser that is built into the exit orifice of the container. To dispense the solution, the user squeezes the bottle forcing solution out of the exit orifice and into his or her eye. Many users have trouble with dispensing eye drops from standard dispensing bottles. The user has a tendency to blink when the drop is about to enter the eye, causing the drop to miss the eye and land on a closed lid. Therefore, eye drop solution is frequently wasted due to the user blinking during the attempted application and the user ends up with eye drop solution streaming down his or her face.

A number of efforts have attempted to resolve the above mentioned problem. Thomas Keen, in his U.S. Pat. No. 4,543,096, discloses a dispenser with an eyelid opening device. The user is required to place a pair of lid spreading arms dangerously close to his eye and then to press a lever arm to keep the eyelids apart. Thomas Sherman, in his U.S. Pat. No. 6,371,945, discloses an attachment for a bottle that includes a ring intended to help align the bottle with the eye. However, no attempt is made to hold the eyelid open. Gary Campagna, in his U.S. Pat. No. 3,934,590, shows a tripod like device for aligning the solution bottle over the user's eye. No attempt is made to hold the lid open. James Davidian, in his U.S. Pat. No. 6,595,970, shows a device for dispensing eyed drops. He proposes a dispensing arm, one side of which includes an indentation that receives the user's nose, the other side of which accepts a dispensing bottle. The bottle includes a pair of arms which, when squeezed, impinge on the side walls of the bottle forcing solution out of the bottle and into the user's eye. No attempt is made to hold the user's eyelid open. The U.S. Pat. No. 4,692,834 of Julia Clifford et al shows a dispenser that facilitates the user's amount of drops that exit a solution holding bottle. This bottle has retractable apertures that capture and release a drop of solution. James Walsh, in his U.S. Pat. No. 4,927,062, U.S. Pat. Nos. 6,041,978 and 6,010,488 and U.S. Pat. No. 4,834,727 as well as U.S. Pat. No. 5,902,292, all attempt to position an eye drop bottle in a correct location above a person's eye, but none of them includes a means to help hold the user's eye lids in the spread apart, open position. U.S. Pat. No. 4,321,916 discloses an eyelid retractor that is used during ocular surgery or the like. It is not designed to be used by a user of eye drop solution.

None of the above cited inventions safely holds the user's eyelids open while dispensing eye drops from a standard eye drop bottle. Additionally, none of the above mentioned patents allows the user to dispense a portioned amount of eye drop solution in an automatic and repeatable fashion. None of the above cited inventions dispenses a precise amount of eye drop solution and simultaneously holds the user's eyelids open while doing so.

SUMMARY OF THE INVENTION

The primary object of the invention is to provide a holder for an eye drop bottle that includes resilient lid spreading legs.

Another object of the invention is to provide a lid spreading eye drop bottle holder that allows the user to easily attach and detach a standard eye drop bottle to the lid spreading device.

Another object of the invention is to provide a lid spreading eye drop bottle holder that does not interfere with the eye drop bottle tip.

A further object of the invention is to provide a lid spreading eye drop bottle holder that firmly attaches to the eye drop bottle.

Yet another object of the invention is to provide a lid spreading eye drop bottle holder that is inexpensive to manufacture.

Another object of the invention is to provide a lid spreading eye drop bottle holder that automatically dispenses a portioned amount of eye drop solution when the user presses a dispensing button on the device.

Yet another object of the invention is to provide a lid spreading eye drop bottle that flashes an LED light to inform the user that a dispensing action has taken place or is about to take place.

Other objects and advantages of the present invention will become apparent from the following descriptions, taken in connection with the accompanying drawings, wherein, by way of illustration and example, an embodiment of the present invention is disclosed.

In accordance with an embodiment of the invention, there is disclosed a first embodiment of an eye drop bottle holder with resilient legs comprising: an inverted U-shaped shape made from resilient injection molded plastic, the top portion of said inverted U-shape including a centrally located aperture and downwardly facing collar, said collar having internal threads that match the external threads of a standard eye drop bottle containing eye drop solution, the right and left leg of said U-shape each terminating in an outwardly disposed J-shape, the underside of said J-shape covered by a soft rubber-like pad, so that when a user screws said standard eye drop bottle into said threaded collar, the dispensing tip of said eye drop bottle can come into close proximity of the user's eye, and so that the user can cause his or her eye lid to remain open by using the fingers of one hand to squeeze said right and left legs together, then placing the said rubber-like pad of one leg on his or her upper ridge of the orbital eye socket and the said second rubber-like pad of the second leg on the lower ridge of his or her orbital eye socket and then releasing the legs thereby causing the flesh of the user's upper and lower eyelids to be spread apart from each other and remain spread during a standard eye drop solution dispensing event.

In a preferred embodiment of the invention the eye drop bottle is retained within a housing. The housing also includes an electro-mechanical assembly that includes a cam member that pushes on the side of the bottle until a predetermined amount of solution is dispensed, at which point the assembly resets itself automatically to prepare for the next dispensing event. An LED light flashes after each use to confirm that a dispensing event has taken place. Alternately, the LED may flash as a dispensing event is about to take place and stops after the dispensing event has taken place.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
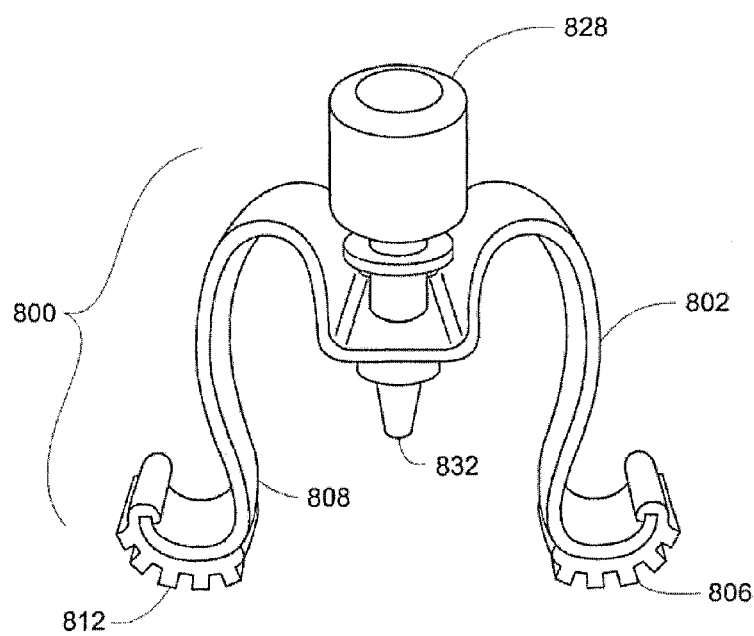
FIG. 1 is a perspective view of the first preferred embodiment of the invention.

Referring now to FIG. 1 we see a front perspective view of the first preferred embodiment of the present eye drop bottle holder invention 800 with a standard eye drop bottle 828 attached. The holder 800 is generally an inverted U-shape that results in two downwardly faced legs 802, 808 that terminate in outwardly disposed J-shaped feet. The feet have rubber-like pads 806, 812 fixedly attached underneath. The legs 802, 808 are injection molded out of resilient plastic such as ABS or Nylon 6. The wall thickness of the legs 802, 808 is such that the spring-like quality of the legs is strong enough to spread a person's upper and lower eye lid, but not strong enough to cause injury to the user's eyelid when the spreading action occurs.

Figure 2:
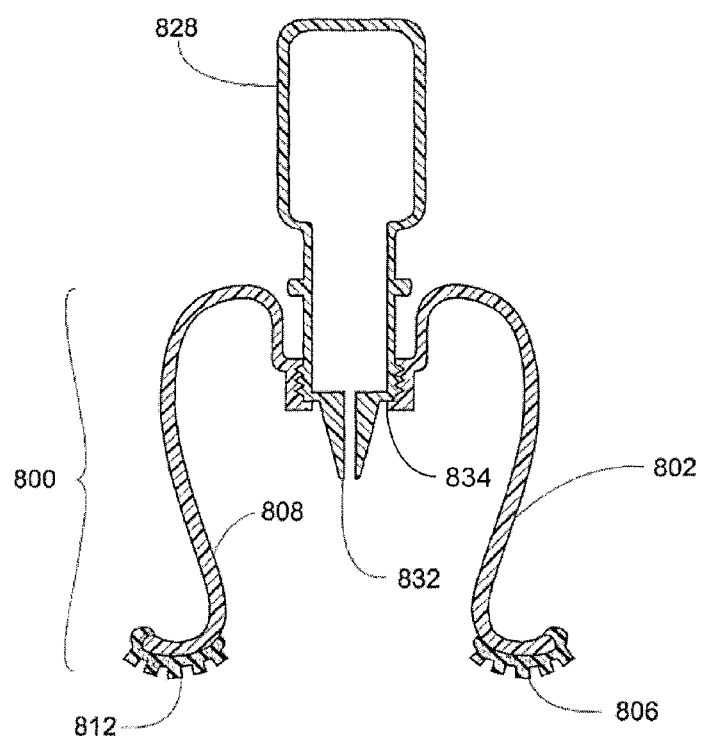
FIG. 2 is a front section view of the first preferred embodiment of the invention.
Figure 3:
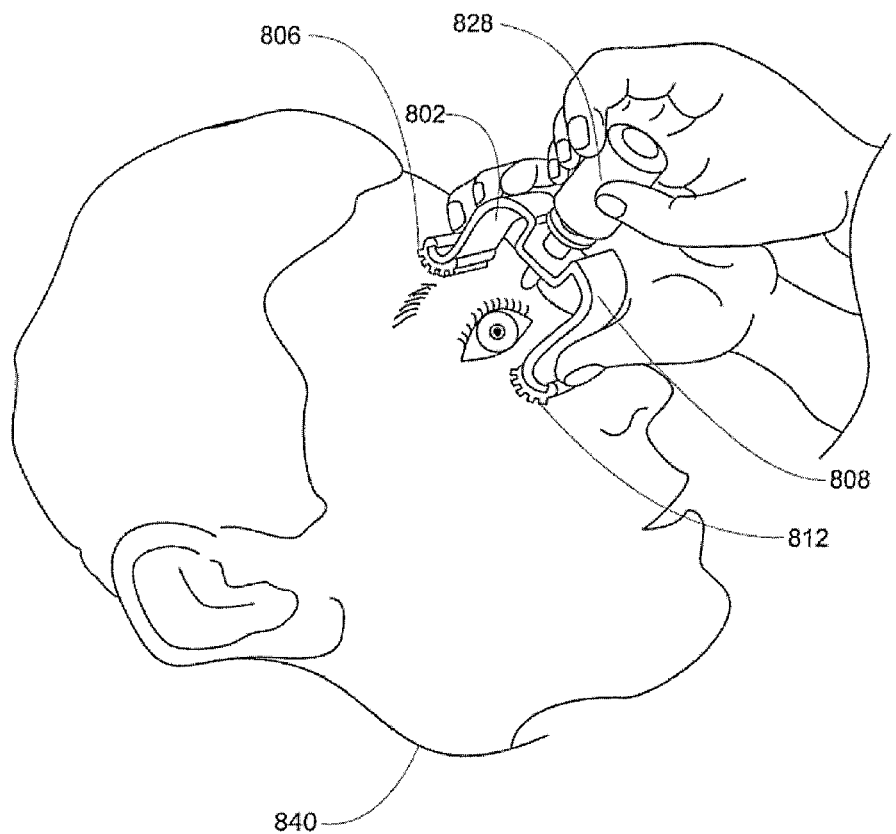
FIG. 3 is a perspective view of a person applying eye drops with the present invention.

FIG. 2 shows a front section view of the invention 800 and bottle 828. Bottle 828 includes standard threads that can engage matching threads 834 located within a centrally located aperture and collar on the top portion of the inverted U-shaped holder 800. The threads on the bottle 828 are normally used for holding the bottle cap (not shown) in place. To use the device 800, the user unscrews the cap of the bottle 828 and screws on the bottle holder 800. Then the user 840 squeezes in on the legs 802, 808 and places the pads 806, 812 of the legs 802, 808 on the upper and lower ridge of the orbital socket as shown in FIG. 3. This places the dispensing tip of bottle 828 at an empirically tested optimal distance from the user's 840 eye. Then the user 840 releases the legs 802, 808 causing the skin around the eye lids and the eye lids themselves to be spread apart. The rubber-like pads 812, 806 protect the user's delicate skin, found on top of the orbital socket, and spare the skin from damage. The user 840 can now squeeze on bottle 828 with his other hand so that a portion of eye drop solution is dispensed directly into the user's eye. Because the lids remain spread during use, there is less ability to blink and therefore more chance that the eye drop solution will find its way to the intended location; the user's eye.

The holder 800 can be sold separately, due to the fact that the majority of over the counter eye drop solutions are packaged in a common shaped bottle with common threads. Or the holder 800 can be packaged along with a bottle of eye drop solution during the manufacturing and packaging process. In this instance, the holder 800 can be sized specifically for the shape of the eye drop solution holding bottle 828 and dispensing tip 832 thereby allowing the bottle 828 to be a different design and shape than the standard eye drop solution bottle now available in stores. The holder 800 is inexpensive and easy to manufacture so that it would be able to be sold at a low price to the consumer.

Figure 4:
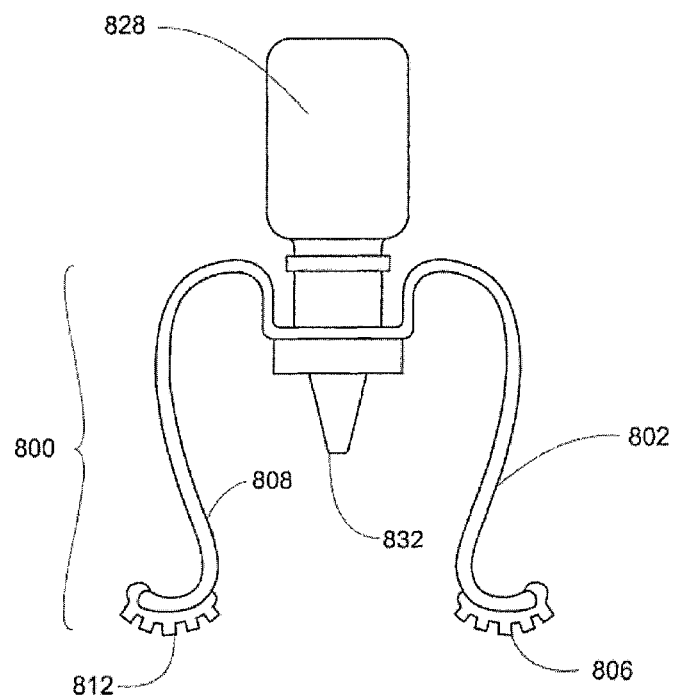
FIG. 4 is a front view the first preferred embodiment of the invention.

FIG. 4 is a front plan view of the first preferred embodiment as described above.

Figure 5:
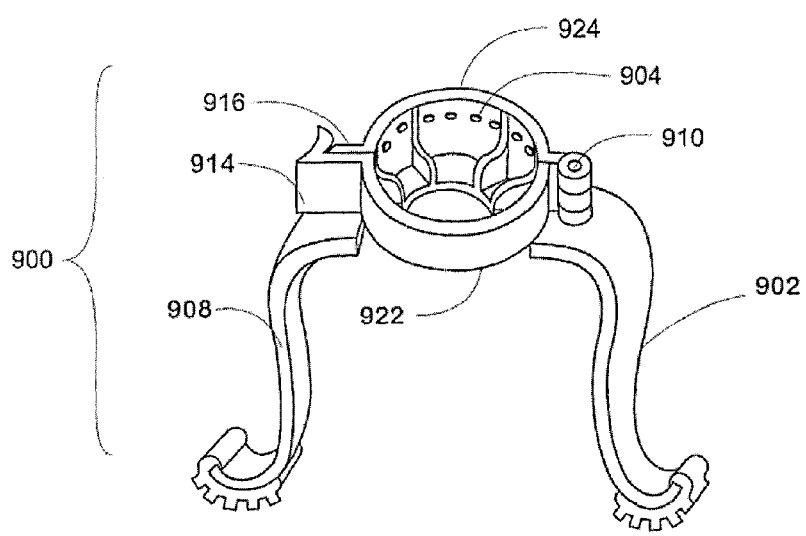
FIG. 5 is a perspective view of a second preferred embodiment of the invention in the closed position.
Figure 6:
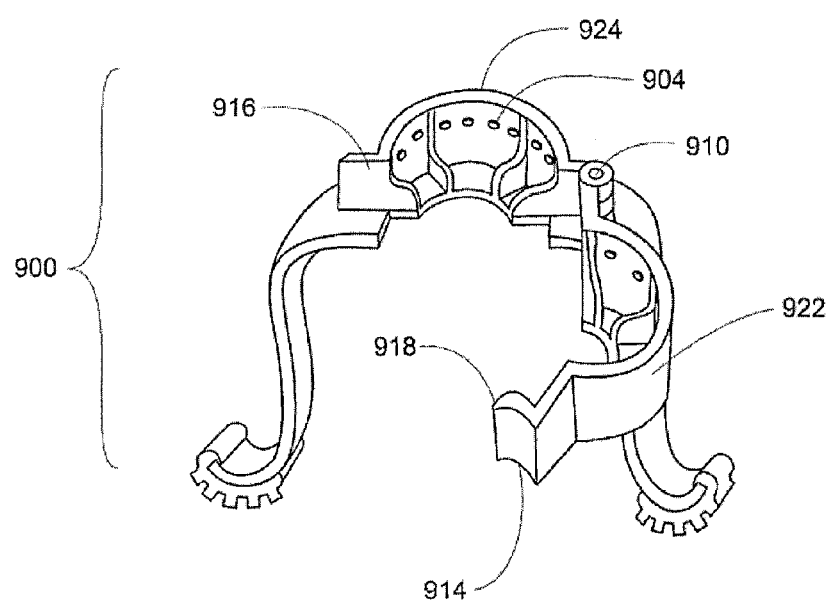
FIG. 6 is a perspective view of the second preferred embodiment of the invention in the open position.
Figure 7:
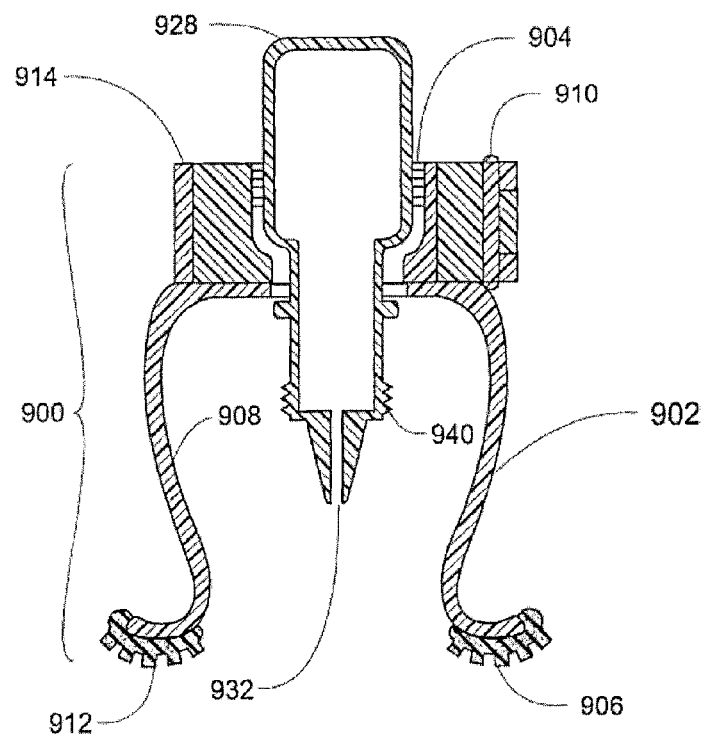
FIG. 7 is a front section view of the second preferred embodiment of the invention.

FIG. 5 is a perspective view of a second preferred embodiment of the present invention 900. In this embodiment two C-shaped members 924, 922 form a cylindrical collar that can firmly hold a standard eye drop bottle. The C-shapes are hinged on one side 910 and snap closed on the other side by tab 916 and snap member 914. The user can swing open C-shape 922 and insert a standard bottle in an upside down position as shown in FIG. 6. Small bumps 904 or other standard gripping means are located on the inner walls of the C-shapes 922, 924 so that when the C-shapes are closed, they firmly grip the bottle held inside as shown in the section view in FIG. 7. The location of the tip of the bottle 932 is an optimal distance from the user's eye during use. Because the threads 940 are accessible after the bottle 928 is placed in the holder 900, the cap 950 of the bottle may be screwed on and off without removing the bottle 928 from the holder 900. Rubber-like pads 906, 912 and the resilient features of the legs 902, 908 are similar to those described in the first embodiment 800.

Figure 8:
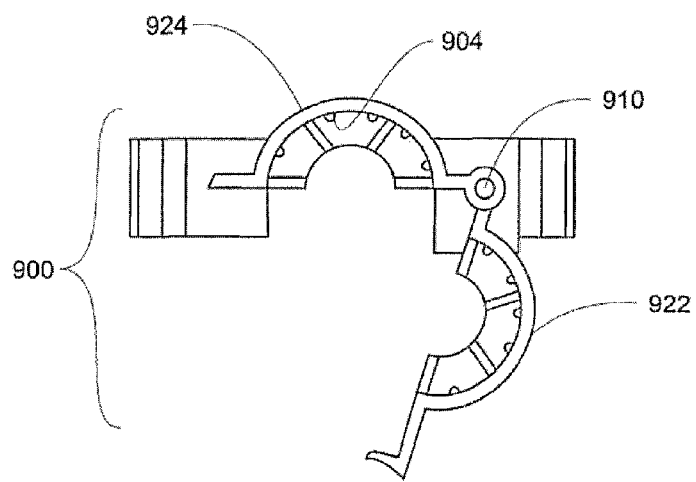
FIG. 8 is a top plan view of the second preferred embodiment of the invention in the open position.

FIG. 8 is a top plan view of the second preferred embodiment 900 in the open position.

Figure 9:
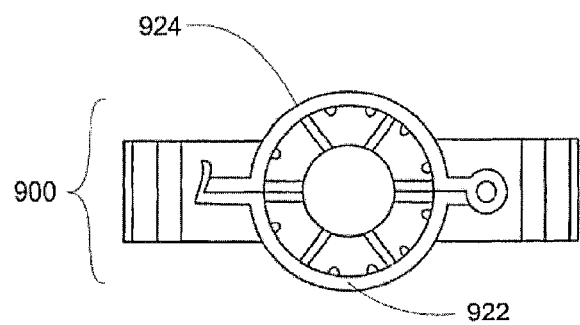
FIG. 9 is a top plan view of the second preferred embodiment of the invention in the closed position.

FIG. 9 is a top plan view of the second preferred embodiment 900 in the closed position.

Figure 10:
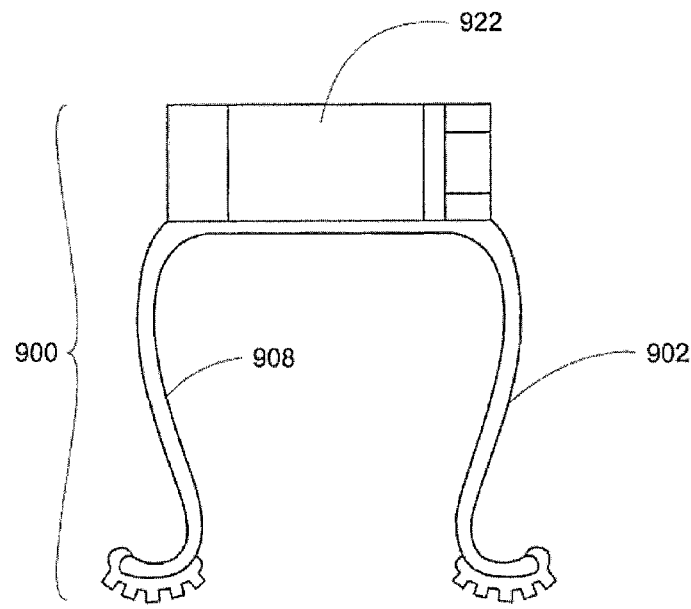
FIG. 10 is front view of the second preferred embodiment of the invention.

FIG. 10 is a front plan view of the second preferred embodiment 900 of the invention.

Figure 11:
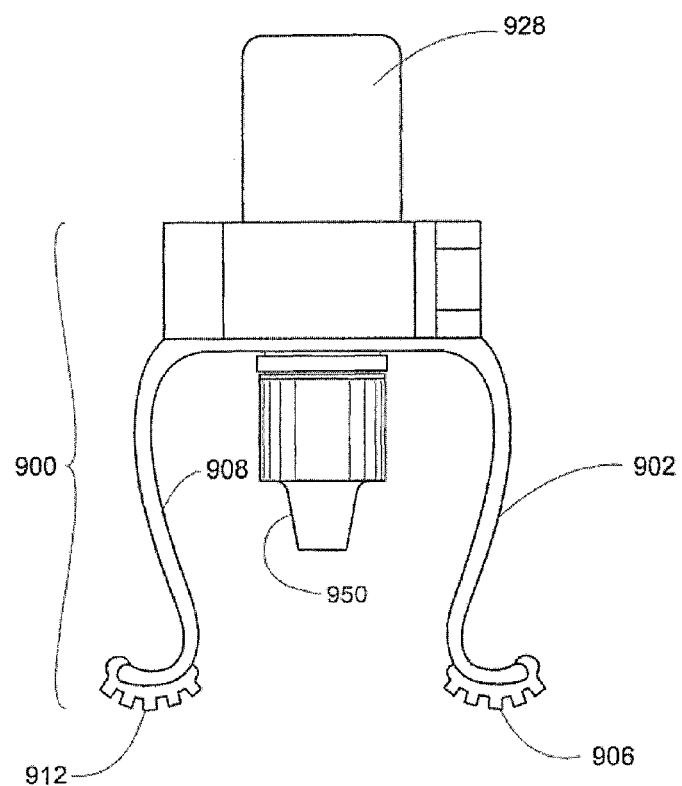
FIG. 11 is a front view of the second preferred embodiment of the invention with an eye drop bottle in place.

FIG. 11 is a front plan view of the second preferred embodiment 900 of the invention with the bottle 928 and cap 950 included.

Figure 12:
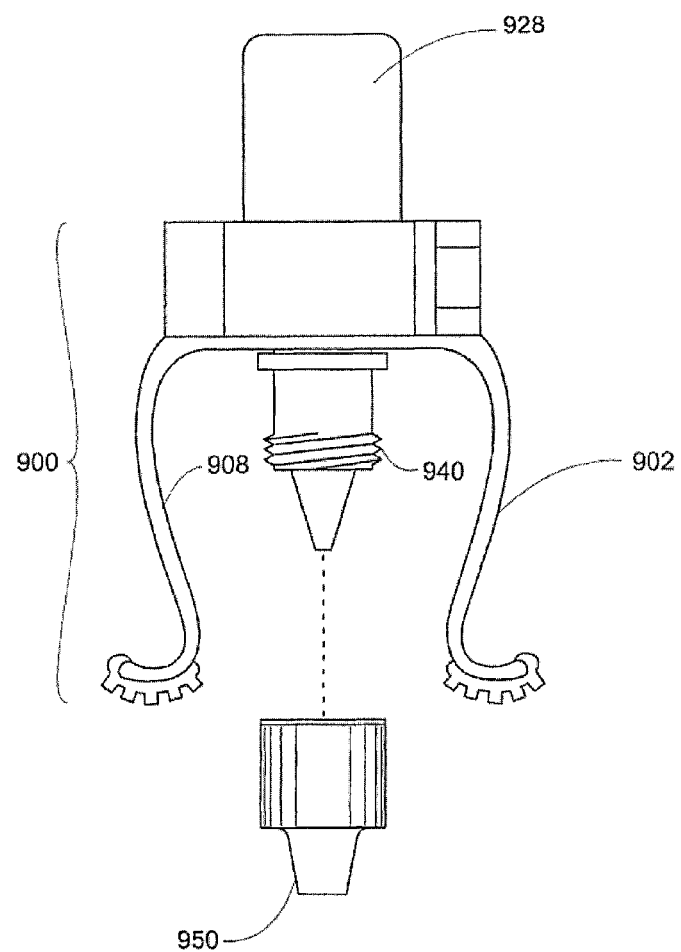
FIG. 12 is a front view of the second preferred embodiment of the invention with an eye drop bottle and bottle cap in place.

FIG. 12 is a front plan view of the second preferred embodiment 900 of the invention with the bottle 928 in place and the cap 950 removed.

Figure 13:
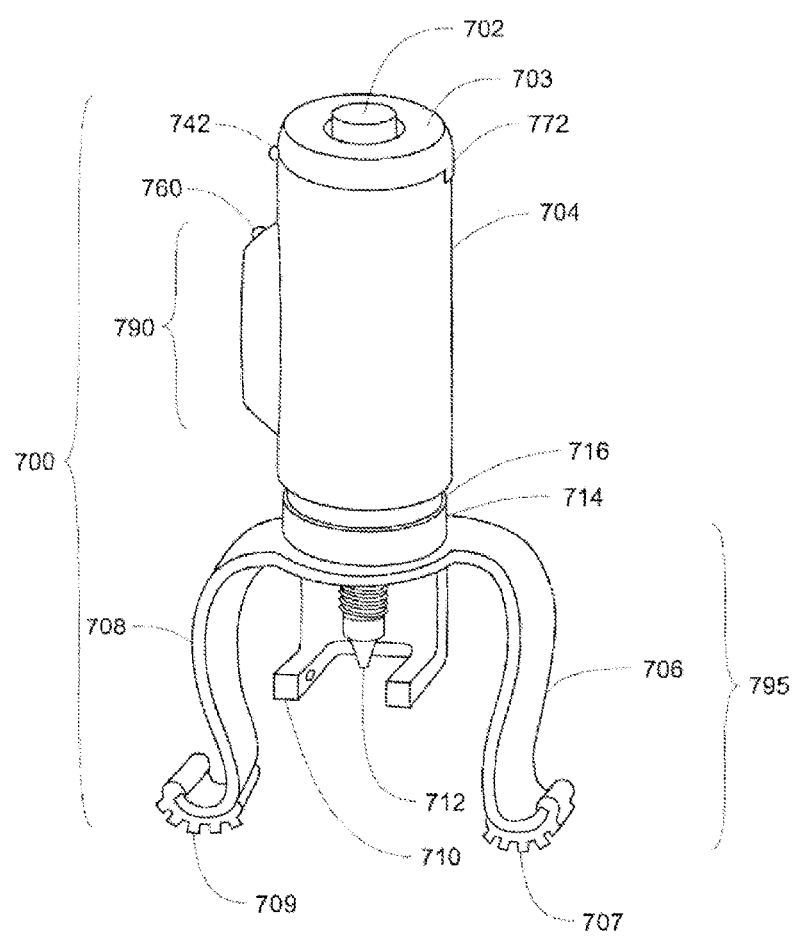
FIG. 13 is a perspective view of a third preferred embodiment that includes a bottle housing and an automatic dispensing assembly.

FIG. 13 shows a third preferred embodiment 700 of the invention. This embodiment 13 may be considered a preferred embodiment because it is the most fool proof of the above described embodiments. With the third embodiment the user simply has to press on top button 702 and a predetermined amount of solution automatically is dispensed into the user's eye. The resilient leg portion 795 of this embodiment works the same was as described in the previous embodiments, with an inverted U-shaped structure that forms two downwardly facing legs 706 & 708 that terminate in outwardly disposed J-shaped feet with rubber-like pads 707 & 709 fixedly attached underneath.

Figure 16:
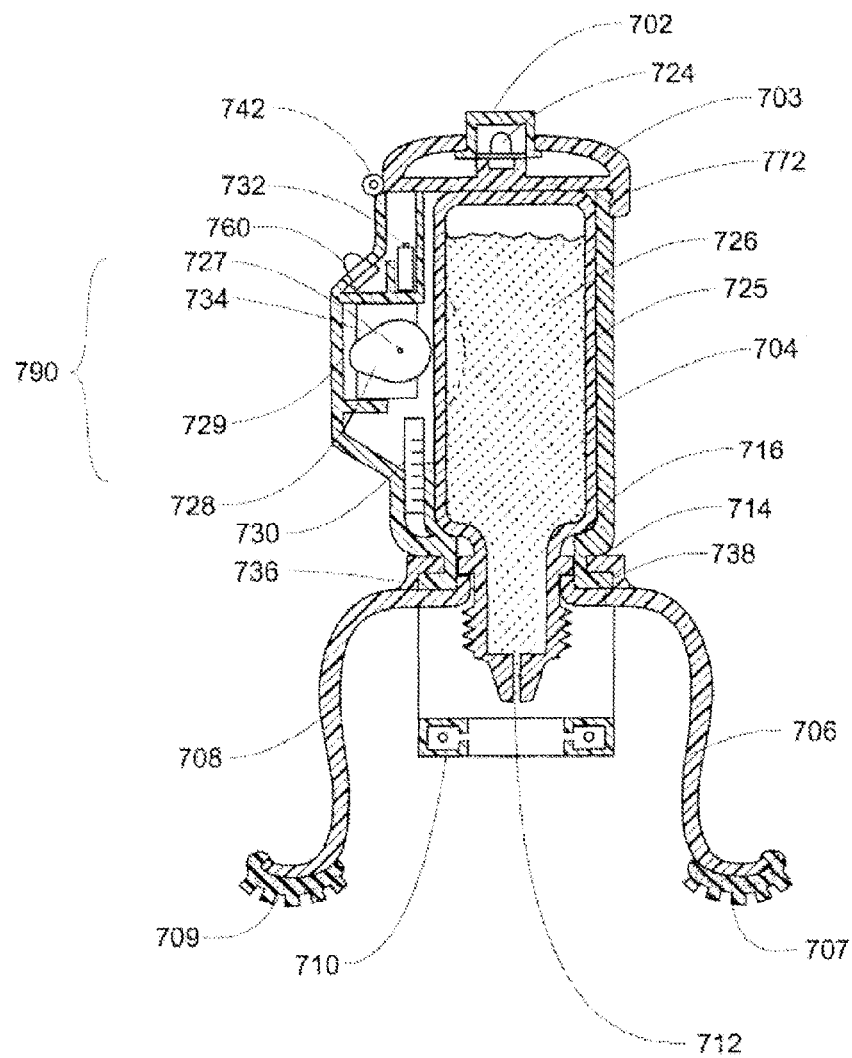
FIG. 16 is a side section view of the third preferred embodiment of the present invention.

In this third embodiment 700 a housing 704 encloses the eye drop solution bottle 725 as shown in side section view of FIG. 16. The housing 704 includes a lid 703 that is attached to the housing 704 by hinge member 742 and held in place by standard clasp member 772. This allows a user to open the housing and replace the bottle if so desired. In this embodiment 700, the user can press dispensing button 702 causing an electromechanical assembly 790 within housing 704 to press on the resilient side wall of the bottle 725, thereby causing a predetermined amount of solution to be dispensed from bottle tip 712. When the solution droplets fall between photo-interrupter sensor 710 an electrical signal is sent to the wall pushing electro-mechanical assembly 790 that caused the droplets to be dispensed and reverses the pushing motion to bring cam 728 back to its starting position so that it is ready for the next dispensing event.

An LED 760 protruding from housing wall 704 illuminates for a short period of time immediately after a dispensing event, giving the user a visual cue that a drop has been dispensed.

Figure 14:
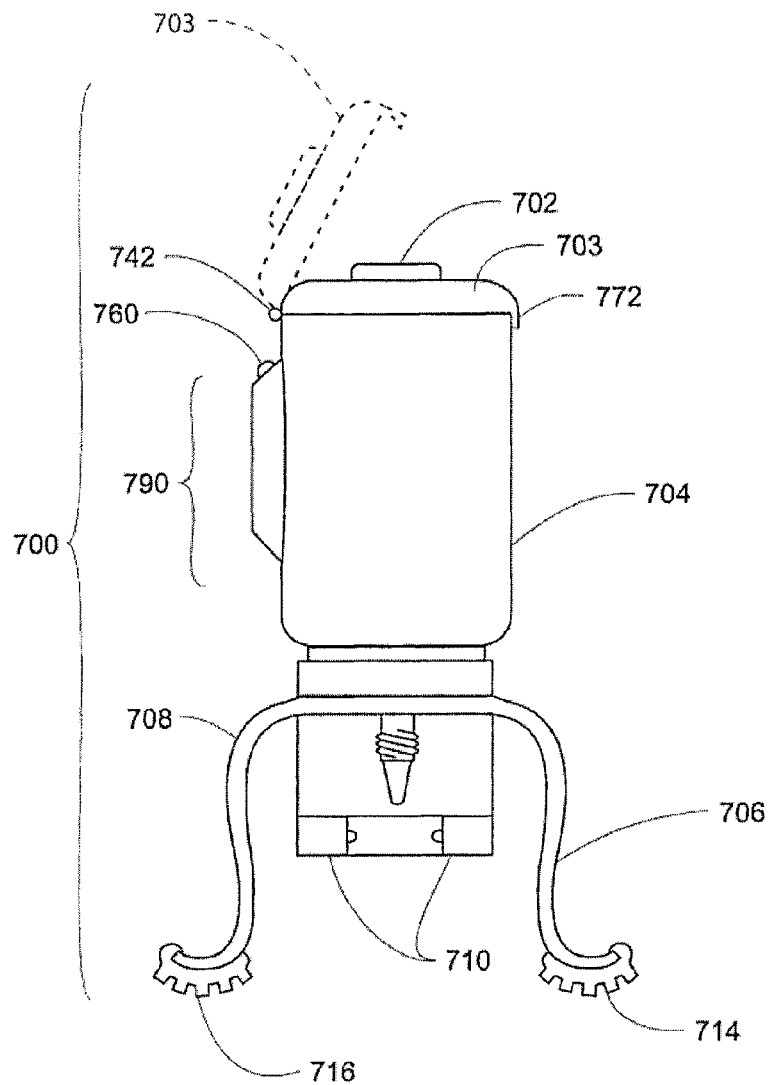
FIG. 14 is a side view of the third preferred embodiment of the present invention.
Figure 15:
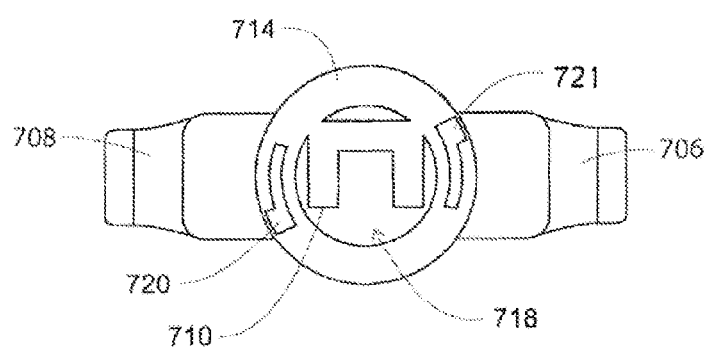
FIG. 15 is a top plan view of the resilient leg portion of the third preferred embodiment of the present invention.
Figure 18:
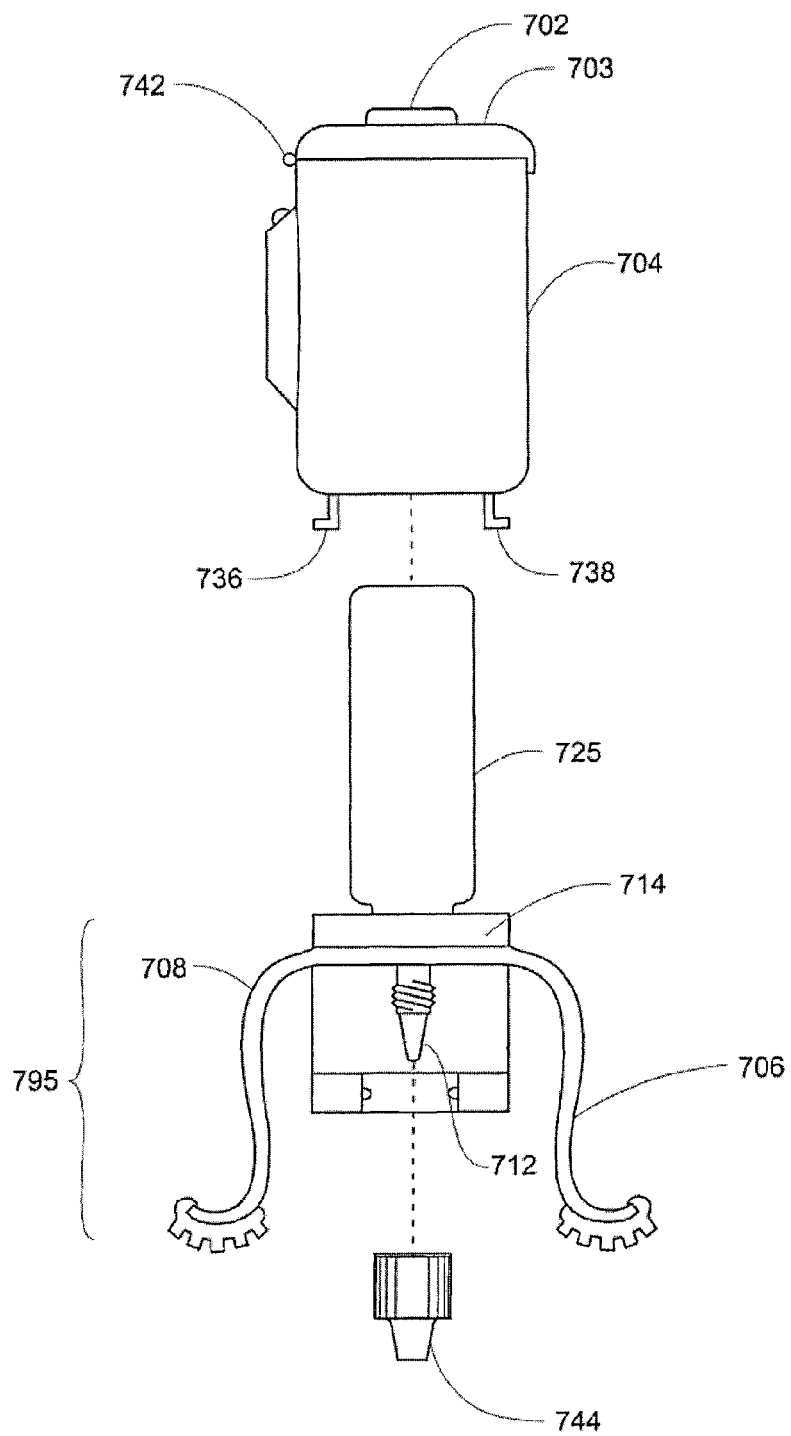
FIG. 18 is an exploded view of the third preferred embodiment of the invention.

FIG. 14 is a side view of the third embodiment 700 of the present invention. The dotted line shows the hinged lid 703 in a raised position, allowing the user to remove or insert an eye drop solution bottle 725 as shown in FIG. 16. The tip 712 and cap threads of the eye drop bottle are exposed so that a standard cap 744 can be screwed on or off in a standard manner as shown in FIG. 18. FIG. 18 also shows housing 704 removed from the leg assembly 795. A pair of outwardly disposed tabs 736, 738 on the underside of the housing 704 can engage with mating slots 720, 721 shown in the top plan view in FIG. 15. The tabs 736, 738 are inserted into the wider sections of the slots 720, 721 and then the entire bottle housing 704 is twisted by the user, causing the tabs 736, 738 to be retained within the collar portion 714 of the leg assembly 795 with shoulder portion 716 of bottle housing 704 nested into collar portion 714. This method of retention is commonly known as a bayonet fit.

FIG. 16 shows a front section view of the third preferred embodiment of the invention. The bottle 725 can be seen residing within housing 704. The neck of the bottle protrudes through an aperture 718 that can be clearly seen in the top plan view of FIG. 15. The droplet sensing photo-interrupter 710 is located just below the level of the bottle tip 712. The sensor 710 is a transmissive photo-interrupter with opposing emitter and detector members housed in a case, providing non-contact sensing of a solution droplet as it travels in its downward trajectory towards the user's eye. A detector such as the Sharp Corp. GP1A57HRJOOF is suitable for the present application; however there are other known detectors that can also be used for this application. LED light 760 is positioned on housing 704, and a motion sensor is positioned within housing 704, the motion sensor configured to detect the positioning of the holder for the release of a drop of solution, LED light 760 configured to flash immediately prior to a dispensing event taking place and LED light 760 configured.

Figure 17:
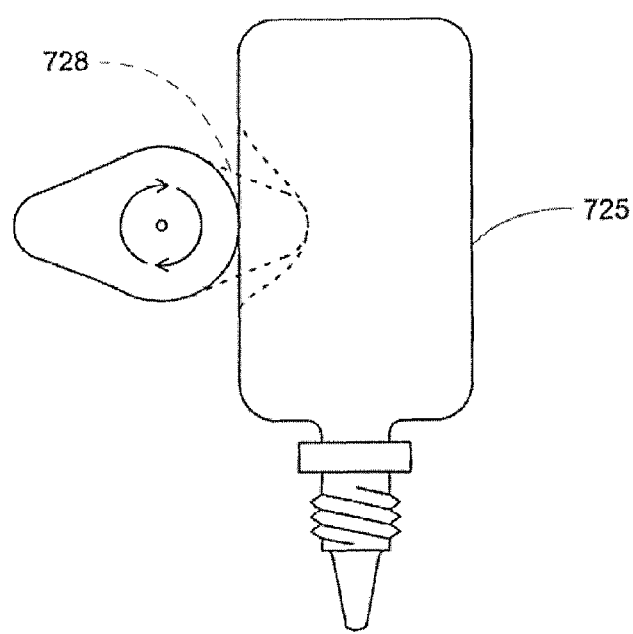
FIG. 17 is a side view of the cam pushing portion of the third preferred embodiment of the present invention.

When the user presses the dispense button 702, it presses on electrical momentary switch 724. The switch 724 sends a signal via standard wires to microprocessor 730 which in turn causes power from battery 732 to be delivered to standard motor and gear assembly 734. A cam member 728 is fixedly attached to the output shaft 727 of the gear assembly 734. When the motor causes the output shaft 727 to turn, it causes cam 728 to rotate and impinge on the resilient wall of the bottle 725. FIG. 17 shows a detailed side view of this action where the dotted lines represent the deformation caused by cam 728 when it is rotated to the extreme position shown, thereby squeezing the bottle 725 as shown by the dotted line representing the wall of the bottle.

When the photo-interrupter device 710 senses the expulsion of a drop 737 of solution 726, it sends an electrical signal to the micro-processor 730 causing the polarity of power going to motor assembly 734 to reverse thereby backing off the cam 728 and reducing pressure on the side wall of the bottle 725. The micro-processor instructs the motor 734 to stop when the cam reaches its start position and turns off switch 729. The cam 728 is then ready for the next dispensing event. Additionally, when the photo-interrupter device 710 senses the expulsion of a drop 737 of solution 726 an LED light 760 turns on and flashes for a approximately five seconds, visually informing the user that a dispensing event has taken place.

Figure 20:
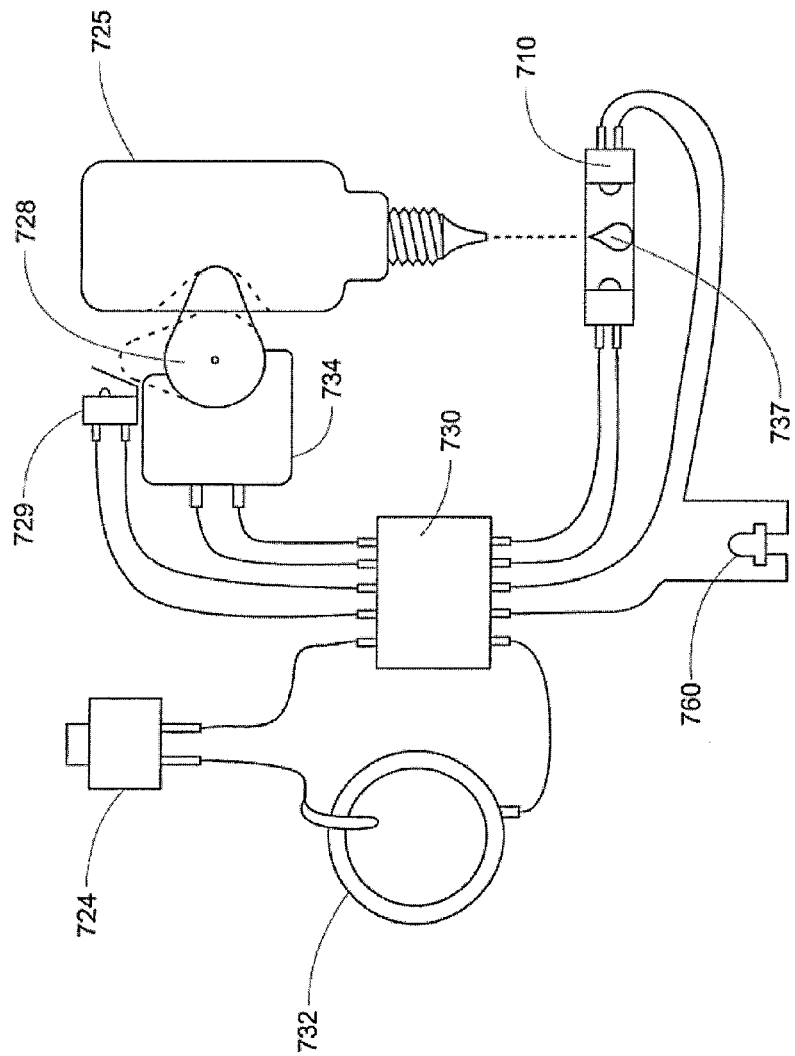
FIG. 20 is a schematic view of the third preferred embodiment of the present invention.
Figure 21:
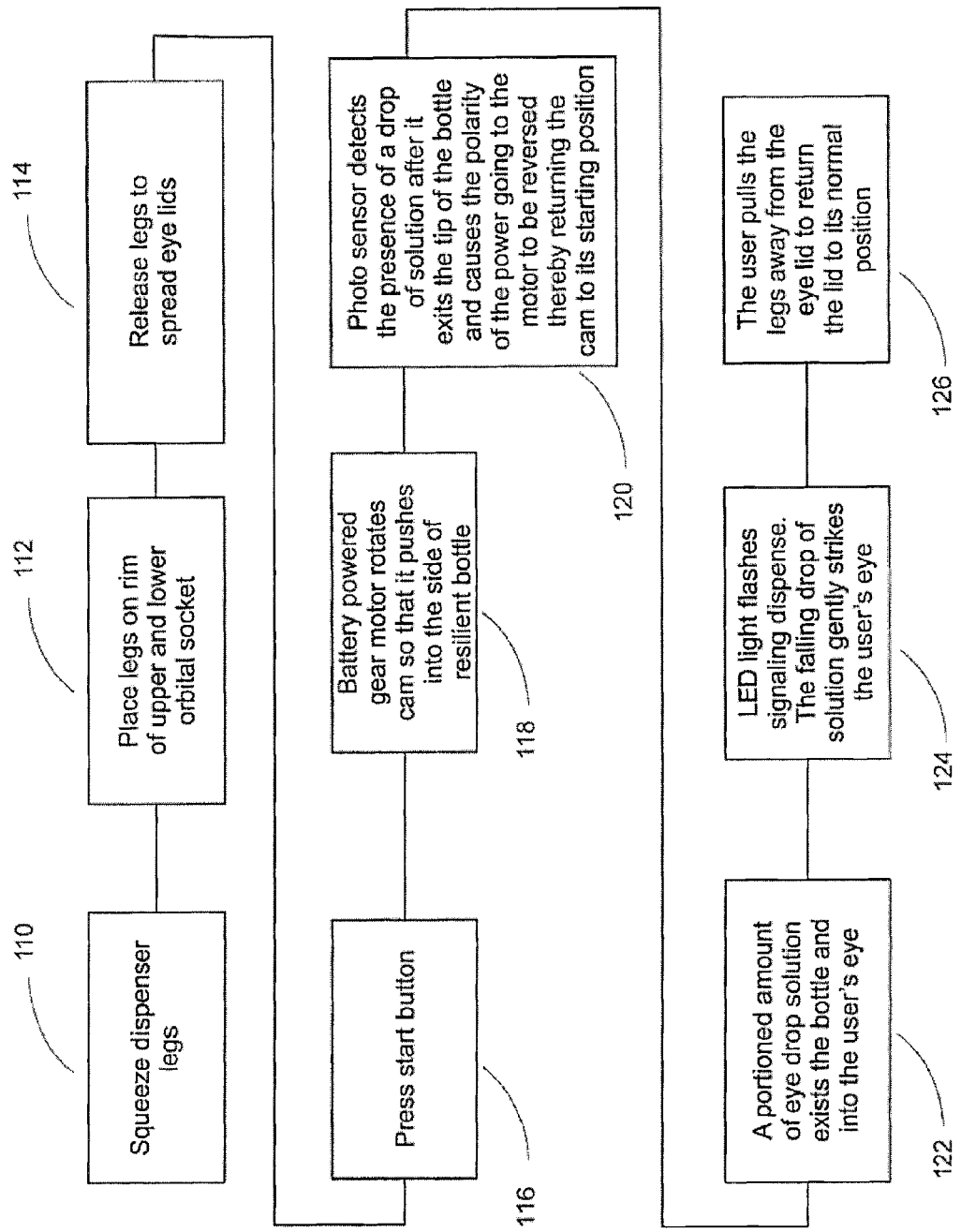
FIG. 21 is a flowchart of the method steps associated with implementing the third preferred embodiment of the present invention.

FIG. 20 shows a schematic view of the components of the third preferred embodiment as described above. FIG. 21 shows a block diagram of the steps involved in a person using the third embodiment as described above. Step 110 involves squeezing the dispenser legs followed by Step 112 wherein the user places the legs of the device on the rim of the upper and lower orbital socket. At Step 114 the user releases the legs to spread the eye lids and at Step 116 presses the start button. The battery powered gear motor rotates the cam so that it pushes into the side of the resilient bottle at Step 118. Step 120 follows wherein the photo sensor detects a drop of solution after it exits the tip of the bottle and causes the polarity of the power going to the motor to be reversed thereby returning the cam to its starting position. This also corresponds to Step 122 wherein a portioned amount of eyedrop solution exits the bottle and into the user's eye. The LED light flashes signaling a dispense event at Step 124 and the falling drop of solution gently strikes the user's eye. Finally, at Step 126 the user pulls the legs of the device away from the eye lid to return the lid to its normal position.

Figure 19:
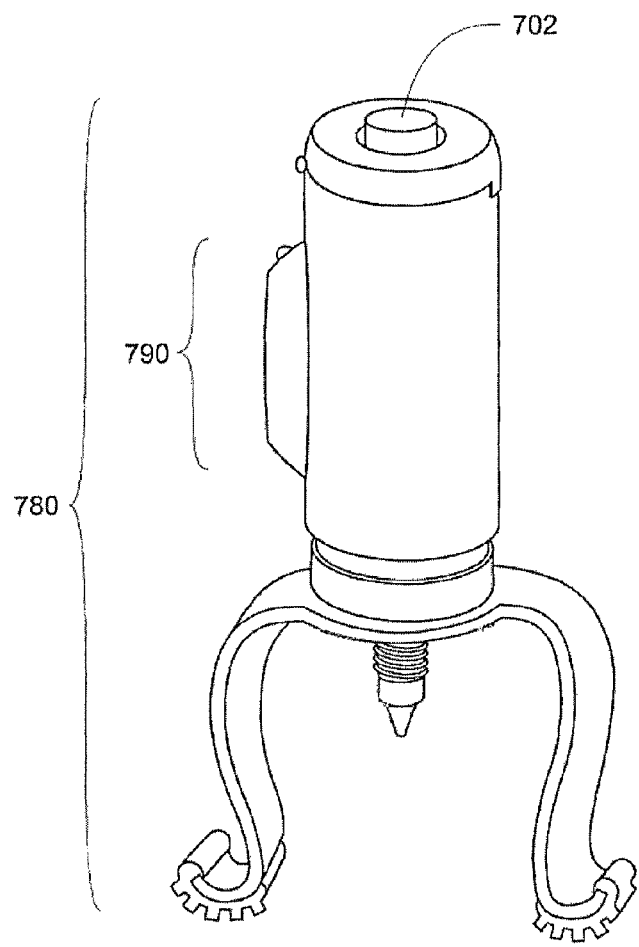
FIG. 19 is a perspective view of the third preferred embodiment of the present invention without the drop sensing photo-interrupter (a fourth preferred embodiment).

FIG. 19 shows a fourth preferred embodiment 780 of the present invention which is similar to the third embodiment 700 except that the droplet sensing photo-interrupter 710 is not included. In this embodiment 780, The user presses on dispense button 702 and when he or she feels the drop of solution hit the eye, he or she removes their finger from the dispense button 702 thereby causing the reversing action of electro-mechanical assembly 790, described in the third embodiment, to take place and bring the cam 728 back to its start position.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An eyedrop delivery system for use in conjunction with a quantity of eyedrop solution contained within a bottle of standard configuration having a bottle neck, a side wall, and a dispensing tip, the delivery system comprising:
   (a) a U-shaped member comprising a shaped band of resilient material, comprising a pair of resilient legs and a mid-section connecting the pair of resilient legs, the mid-section defining an aperture through the U-shaped member;
   (b) a collar positioned in conjunction with the mid-section defined aperture, the collar generally mateable with the bottle neck;
   (c) wherein each of the resilient legs comprise outwardly disposed J-shaped end sections;
   (d) wherein each of the J-shaped end sections comprise a soft rubber-like surface for contact with the user's skin;
   (e) a bottle housing; and
   (f) a battery powered, microprocessor controlled, motor and gear assembly, the motor and gear assembly further comprising a pusher cam positioned to press on the side wall of the bottle, and an electrical dispense button located through a wall of the housing wherein the user activates the motor and gear assembly by pushing the dispense button, and wherein the pusher cam returns to an original start position when the user releases the dispense button;
   wherein the bottle of standard configuration is inserted into the collar so as to position the dispensing tip of the bottle centrally between the pair of resilient legs and the user squeezes the resilient legs together, places the soft rubber-like surfaces of the J-shaped leg end sections against the upper and lower ridges of the user's orbital eye socket and then releases the legs thereby causing the user's upper and lower eyelids to be spread apart from each other and remain spread during eye drop dispensing.

2. The eye drop delivery system of claim 1 further comprising a photo sensor positioned adjacent the dispensing tip of the bottle, the photo sensor capable of detecting a release of a drop of solution and signaling the microprocessor to reverse the motor and gear assembly to direct the cam to return to the original start position.

3. The eye drop delivery system of claim 2 further comprising an LED light positioned on the housing, the LED light configured to flash after a dispensing event has taken place.

4. The eye drop delivery system of claim 2 further comprising an LED light positioned on the housing, and a motion sensor positioned within the housing, the motion sensor configured to detect the positioning of the holder for the release of a drop of solution, the LED light configured to flash immediately prior to a dispensing event taking place and the LED light configured to turn off after the dispensing event has taken place.

* * * * *